US012672773B2

(12) United States Patent
Plekhanov

(10) Patent No.: US 12,672,773 B2
(45) Date of Patent: Jul. 7, 2026

(54) ASTIGMATISM TESTING APPARATUS AND METHOD OF USE

(71) Applicant: Alexander Plekhanov, Portland, OR (US)

(72) Inventor: Alexander Plekhanov, Portland, OR (US)

( * ) Notice: Subject to any disclaimer, the term of this patent is extended or adjusted under 35 U.S.C. 154(b) by 606 days.

(21) Appl. No.: 18/169,133

(22) Filed: Feb. 14, 2023

(65) Prior Publication Data

US 2023/0263387 A1     Aug. 24, 2023

Related U.S. Application Data

(60) Provisional application No. 63/312,007, filed on Feb. 19, 2022.

(51) Int. Cl.
| | | |
|---|---|---|
| *A61B 3/00* | (2006.01) | |
| *A61B 3/028* | (2006.01) | |
| *A61B 3/036* | (2006.01) | |
| *A61B 90/00* | (2016.01) | |

(52) U.S. Cl.
CPC ............ *A61B 3/036* (2013.01); *A61B 3/0025* (2013.01); *A61B 3/0033* (2013.01); *A61B 3/0041* (2013.01); *A61B 3/0075* (2013.01); *A61B 3/0285* (2013.01); *A61B 2090/067* (2016.02)

(58) Field of Classification Search
CPC ..... A61B 3/036; A61B 3/0025; A61B 3/0033; A61B 3/0041; A61B 3/0075; A61B 3/0285; A61B 2090/067; A61B 3/04; A61B 3/028
See application file for complete search history.

(56) References Cited

U.S. PATENT DOCUMENTS

| | | | | | |
|---|---|---|---|---|---|
| 4,185,896 A | * | 1/1980 | Buhler | ................... | A61B 3/036 |
| | | | | | 351/234 |
| 4,385,813 A | * | 5/1983 | Klein | ................... | A61B 3/0285 |
| | | | | | 351/217 |
| 4,436,390 A | * | 3/1984 | Aoki | ................... | A61B 3/0285 |
| | | | | | 351/234 |
| 5,566,087 A | * | 10/1996 | Voigt | ................... | H04N 23/661 |
| | | | | | 348/E5.042 |
| 5,617,260 A | * | 4/1997 | McNiven | ................. | G02B 7/16 |
| | | | | | 359/821 |
| 9,671,618 B2 | * | 6/2017 | Allione | ................. | G02C 7/061 |

(Continued)

*Primary Examiner* — Bumsuk Won
*Assistant Examiner* — John Curtis Sipes
(74) *Attorney, Agent, or Firm* — Mark S Hubert

(57) ABSTRACT

A subjective refractor apparatus for astigmatism testing allowing observation along an optical observation axis with an optical vision correction of variable power. The apparatus allows a patient's use of a tactile input device to control the rotary movement of rotatable optical elements with cylindrical power, varying the angular position of the optical elements to adjust the total cylindrical power and orientation of the cylinder axis of the resulting optical system. The tactile input device is capable of receiving input in two or more dimensions, with each dimension of input controlling the rotary movement of a single cylindrical optical element to adjust the combined cylindrical optical power of the two optical elements. The optical elements position readings may be sensed by rotational position sensors and sent to an operationally connected microprocessor for interpretation and display.

13 Claims, 5 Drawing Sheets

(56)          References Cited

U.S. PATENT DOCUMENTS

2013/0127835 A1* 5/2013 Wang ................... G09G 3/3622
                                                        345/87
2016/0331226 A1* 11/2016 Nauche ................... G02B 3/14
2018/0078131 A1* 3/2018 Durr ...................... A61B 3/113

* cited by examiner

ASTIGMATISM TESTING APPARATUS AND METHOD OF USE

CROSS-REFERENCE TO RELATED APPLICATIONS

THIS APPLICATION CLAIMS THE BENEFIT OF U.S. PROVISIONAL PATENT APPLICATION NO. 63/312,007 FILED FEB. 19, 2022, WHICH IS INCORPORATED BY REFERENCE HEREIN IN ITS ENTIRETY.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to refractors in the field of optometry, and more particularly to a subjective refraction device used in a visual compensation test, and its method of use.

BACKGROUND

Astigmatism is a type of refractive error caused by rotational asymmetry in the eye's refractive power. This results in distorted or blurred vision at any distance. The underlying mechanism involves an irregular curvature of the cornea or abnormalities in the lens of the eye that limit the ability of the eye to simultaneously focus light rays originating from the same point source, but lying in different meridional planes of the eye lens, on the retina, rather than in front of, or behind it. 40-60% of the population has some degree of astigmatism. The level and type of astigmatism is determined by an optometrist or ophthalmologist at the same time when they examine the acuity of a patient's vision. Using a phoropter, the practitioner first determines a spherical optical power for patient's distance-specific vision correction, and then tests for astigmatism using a cylindrical refractor and Jackson cross-cylinder lens to determine the corrective cylindrical optical power and the angle of cylinder orientation.

Refractors are well-known ophthalmic instruments used for determining the proper lens characteristics necessary to correct defective vision of a patient. A refractor typically includes a right eye lens battery and a left eye lens battery, each enabling the practitioner to place various corrective lenses in alignment with one of the patient's eyes. Each of the lens batteries is alike and each includes a spherical lens assembly and a cylindrical lens assembly, with each assembly including a plurality of discrete, progressively powered lenses. A practitioner selects specific lenses and places them in alignment with the patient's eye to determine the proper lens values for correcting the patient's vision.

However, such a procedure is suboptimal, requiring consistent intervention of a practitioner to operate. Furthermore, this procedure involves lens changes, resulting in undesired discrete transitions in corrective power, and is particularly time consuming.

Henceforth, an apparatus for the testing of astigmatism that requires little or no input by an optometry practitioner, can be manipulated by the patient, and corrects vision with non-discrete refraction adjustment would fulfill a long felt need in the optometry industry. This new invention utilizes and combines known and new technologies in a unique and novel configuration to overcome the aforementioned problems and accomplish the simplification of the optometry procedure.

BRIEF SUMMARY

In accordance with various embodiments, a subjective refraction apparatus for astigmatism testing with an optical vision correction of variable power is provided. The apparatus is designed to require minimal physician involvement, instead accepting a patient's use of a direct input device (such as a mouse or trackpad) to control the subjective refraction apparatus so as to facilitate the determination of the corrective lens prescription.

Various modifications and additions can be made to the embodiments discussed without departing from the scope of the invention. For example, while the embodiments described above refer to particular features, the scope of this invention also includes embodiments having different combination of features and embodiments that do not include all of the above-described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components.

DETAILED DESCRIPTION

Figure 1:
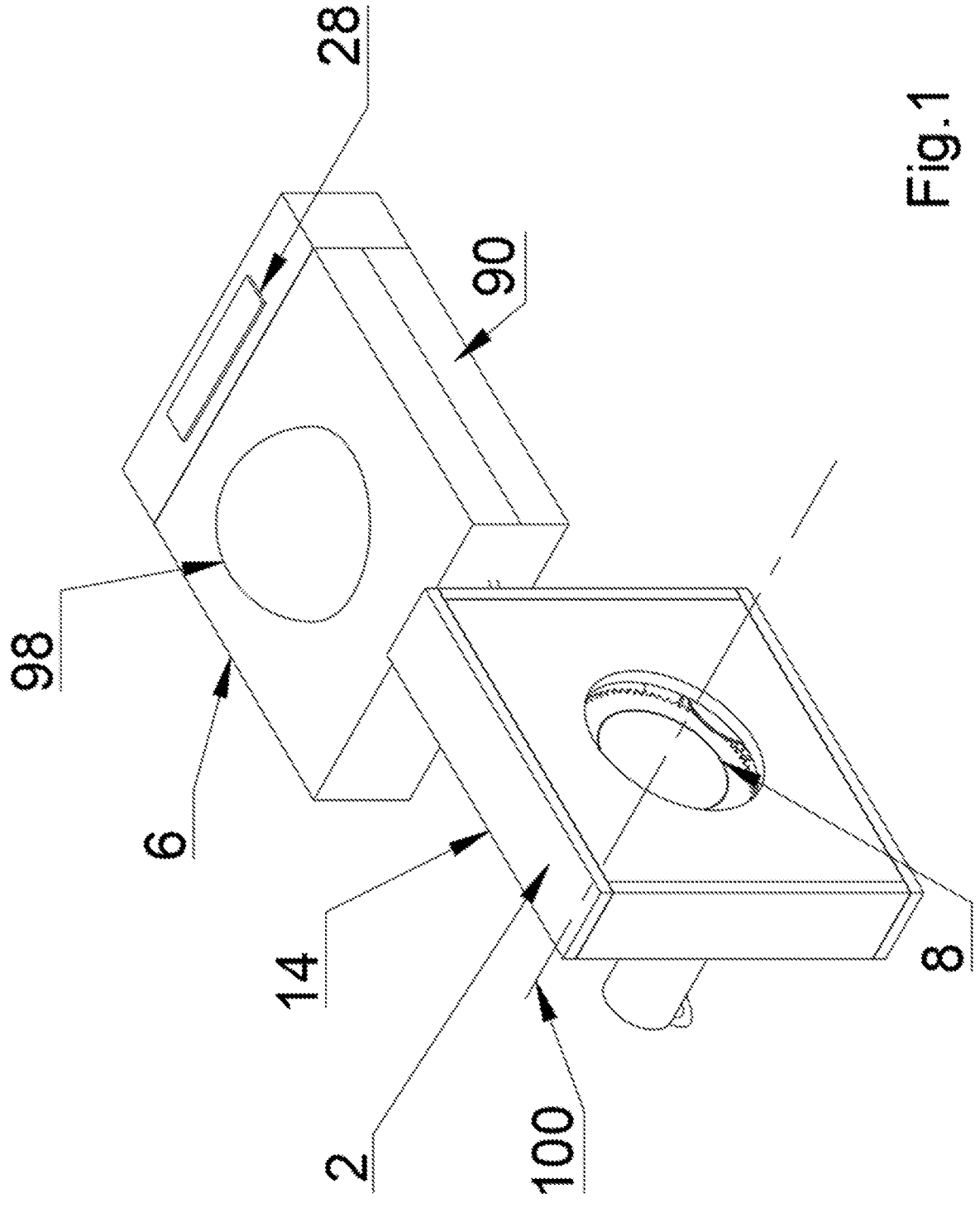
FIG. 1 is an isometric view of the astigmatism testing apparatus with its preferred method of control.

Reference will now be made in detail to embodiments of the inventive concept, examples of which are illustrated in the accompanying drawings. The accompanying drawings are not necessarily drawn to scale. In the following detailed description, numerous specific details are set forth to enable a thorough understanding of the inventive concept. It should be understood, however, that persons having ordinary skill in the art may practice the inventive concept without these specific details. The described examples are provided for illustrative purposes and are not intended to limit the scope of the invention.

It will be understood that, although the terms first, second, etc. may be used herein to describe various elements, these elements should not be limited by these terms. These terms are only used to distinguish one element from another. For example, a first attachment could be termed a second attachment, and, similarly, a second attachment could be termed a first attachment, without departing from the scope of the inventive concept.

It will be understood that when an element or layer is referred to as being "on," "coupled to," or "connected to"

another element or layer, it can be directly on, directly coupled to or directly connected to the other element or layer, or intervening elements or layers may be present. In contrast, when an element is referred to as being "directly on," "directly coupled to," or "directly connected to" another element or layer, there are no intervening elements or layers present. Like numbers refer to like elements throughout. As used herein, the term "and/or" includes any and all combinations of one or more of the associated listed items.

The terminology used in the description of the inventive concept herein is for the purpose of describing particular embodiments only and is not intended to be limiting of the inventive concept. As used in the description of the inventive concept and the appended claims, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. It will be further understood that the terms "alternative", "alternatively", and their derivatives as used herein are intended to also mean "additional", "additionally", and their derivatives.

As used herein, the term "optical power" is the degree to which an optical element is able to make light rays converge or diverge. It is expressed in diopters and corresponds to the inverse of focal length in meters.

As used herein, the term "spherical power" is spoken of when the optical power is the same in all the meridian planes of the lens (rotational symmetry about the optical axis).

As used herein, the term "astigmatism" is spoken of when the optical power varies depending on the meridian of the lens. In the case of an astigmatic optical element, "cylindrical power" is spoken of as the difference between the maximum optical power along a first meridian and the minimum optical power along a second meridian. This is the case for toric or cylindrical lenses.

As used herein, the term "cylindrical lenses" are a type of lens that have differing radii of curvature in the planes of X and Y axes, causing the lens to have a cylindrical or semi-cylindrical shape, and image magnification in the direction of only a single axis. Cylindrical lenses are commonly used as laser line generators, or to adjust image height size or correct for astigmatism in imaging systems. As used herein, the term "cylindrical lens" may also mean a toric lens.

As used herein, the terms "astigmatism testing apparatus" and "subjective refractor apparatus" identify the same device.

The present invention relates to a novel design for a subjective refraction apparatus 2 (astigmatism testing apparatus) allowing observation along the optical axis 100 with an optical vision correction of variable power. The apparatus 2 is particularly directed towards a patient's use of a manual control input device 6 to control the rotary movement of rotatable optical elements 16 or 20 with cylindrical power, varying the angular position of the optical elements 16 and 20 to adjust the total cylindrical power and orientation of the cylinder axis of the resulting optical system. Such a manual control input device 6 can be capable of receiving input in two or more dimensions, with each dimension of input controlling the rotary movement of a single cylindrical optical element 16 or 20 to adjust the combined cylindrical optical power of the two optical elements 8. Examples of suitable manual control input devices 6 include but are not limited to: knobs with two degrees of freedom, joysticks, trackballs, trackpads, computer mice, and the like, or multiple one-dimensional input devices. Input devices may rely on mechanical, electrical, electronic, electromagnetic, electrooptical, or otherwise electronic principles of operation and control, or a combination thereof, as is well known in the computer industry. The optical elements position readings may be sensed by rotational position sensors or rotation step counters and sent to an operationally connected microprocessor for interpretation and cross reference to a relational database or calculation of the resulting combined cylindrical power and cylinder axis position, which could then be output to a visual display or used for further computational processing. In an even simpler embodiment, there may be indexing lines or scale on any part of the rotational gearing and a pointing needle, mark, or other reference element on any stationary part of the apparatus, or vice versa, to enable the readout of the rotational position of each of the optical elements 8.

Looking at FIGS. 1-5 it can best be seen that the preferred embodiment of the astigmatism testing apparatus 2 is comprised of a manual input device 6, a housing 14 that contains a first rotatable optical element 16, a first rotational unit 18, a second rotatable optical element 20, a second rotational unit 22, a first rotational shaft 24, and a second rotational shaft 26. (It is to be noted that the manual control input device may be connected to a computing device and/or visual display terminal to show the astigmatism correction readings, or as in the preferred embodiment, it has its own visual display 28.)

Figure 2:
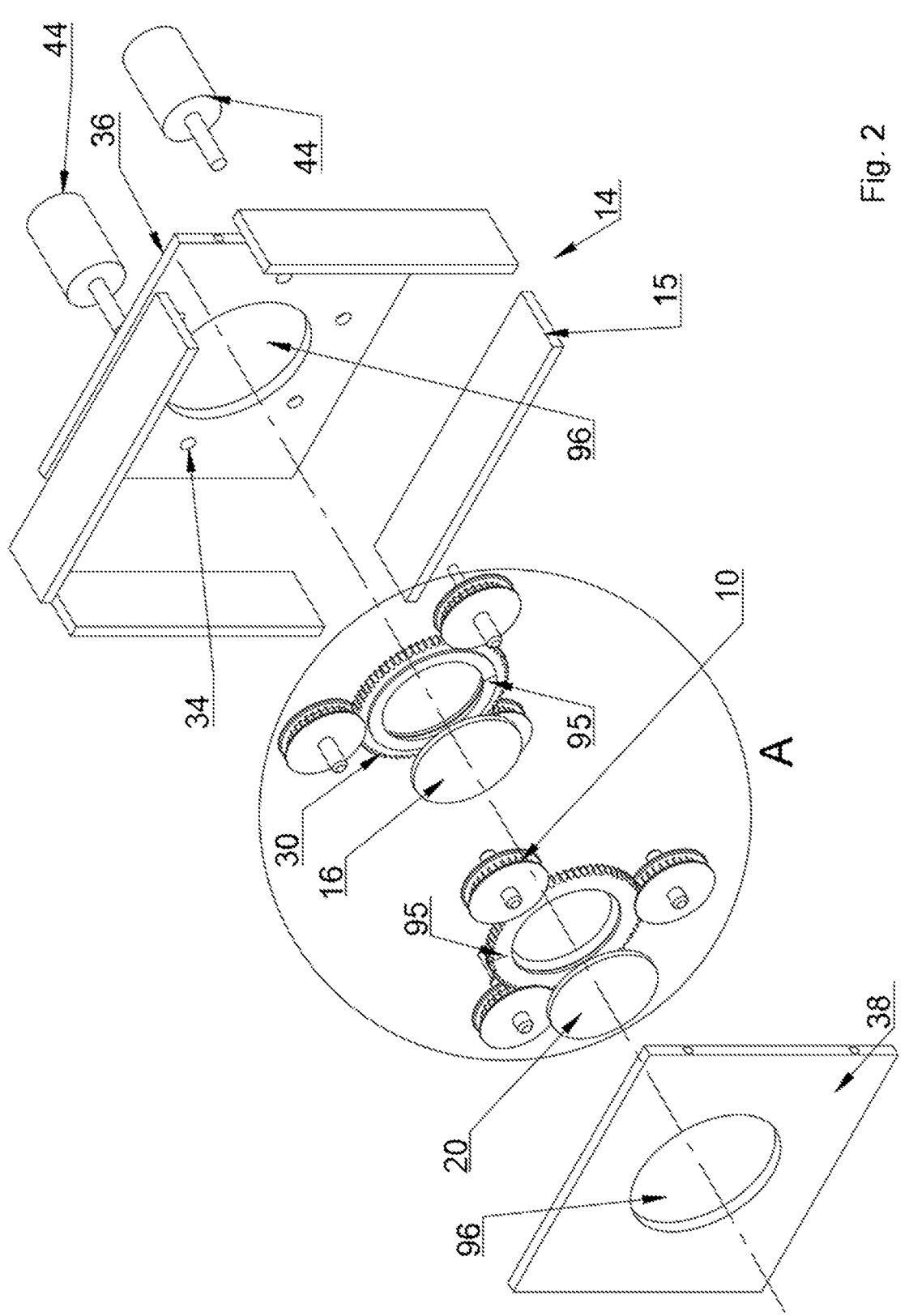
FIG. 2 is an exploded, isometric view of the astigmatism testing apparatus.
Figure 3:
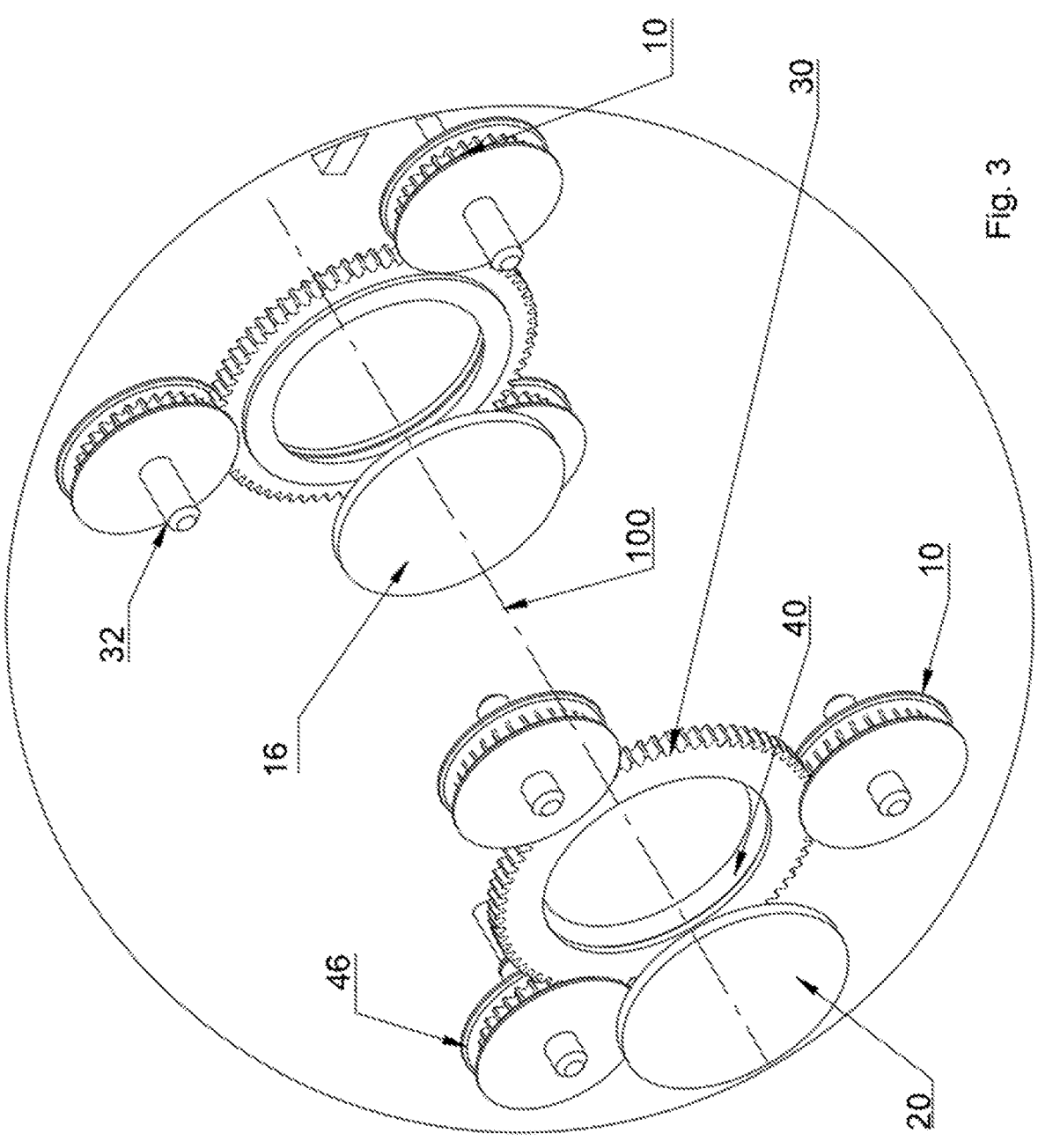
FIG. 3 is an enlarged view of area A of FIG. 2, showing the lens holding design of the astigmatism testing apparatus.
Figure 4:
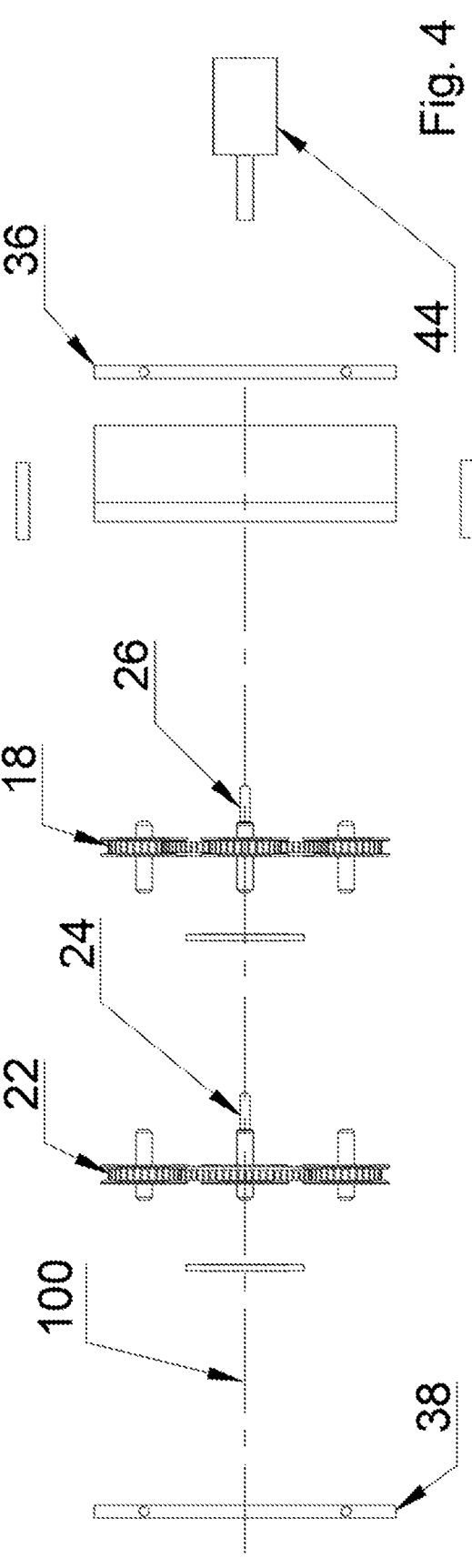
FIG. 4 is an exploded, side view of the astigmatism testing apparatus.
Figure 5:
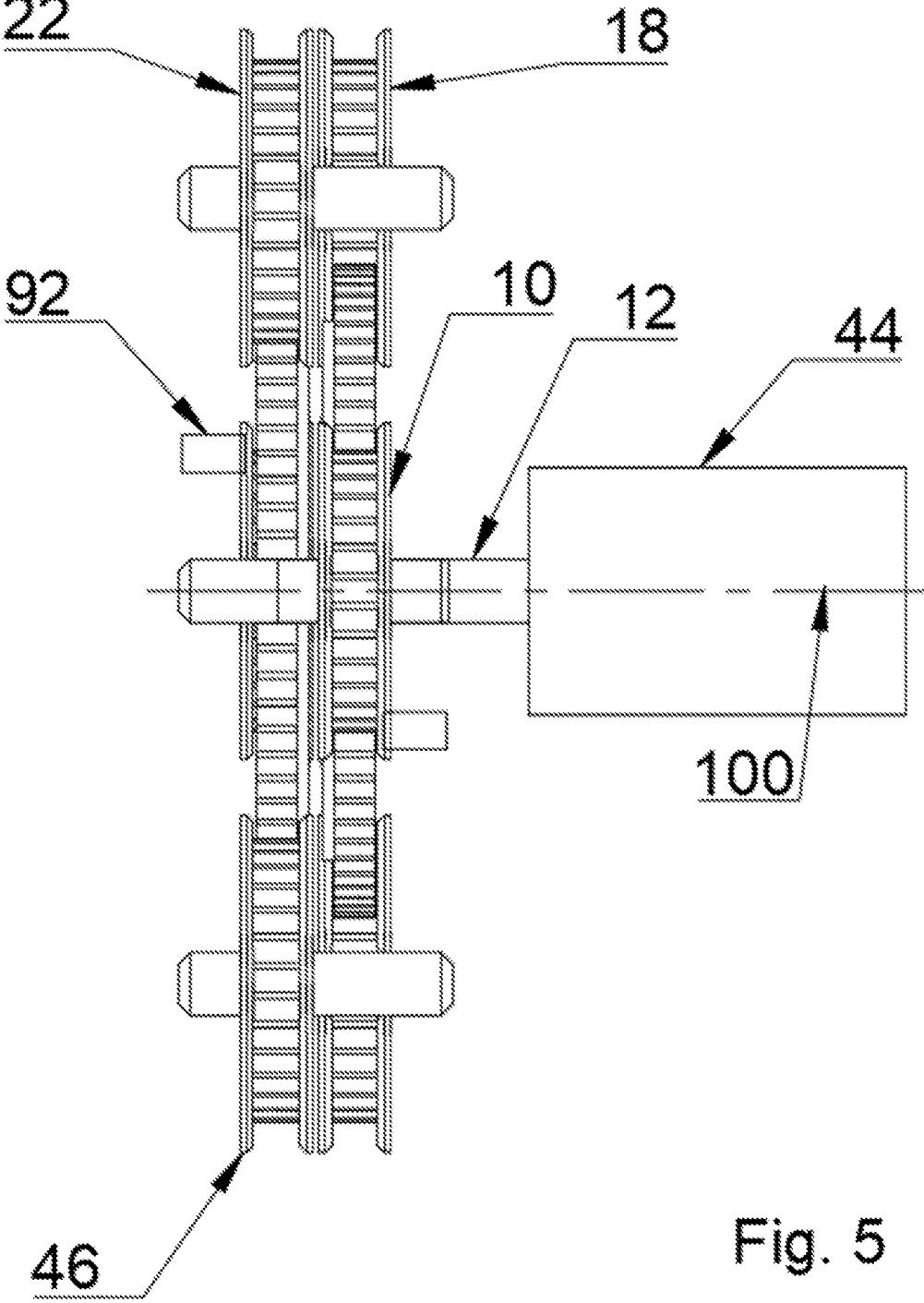
FIG. 5 is a side view of the astigmatism testing apparatus with its housing removed.

Looking at FIG. 2 it can be seen that the housing 14 has an enclosed configuration that internally houses the rotatable optical elements 16 and 20 and their rotational units18 and 22. The housing 14 has a front panel 36 and rear panel 38 held in a space configuration by side panels 15. The front and rear panels 36 and 38, each, have a circular cutout 96 centered on the main rotational axis 100 of the system, which is coincident with the optical axis, thus allowing for viewing through the apparatus in the direction of the optical axis of the system. (In alternate embodiments the housing may not be totally enclosed or even have circular cutouts coincident with the optical axis of the two lenses. The important feature is that the patient's line of sight can be coincident with the optical axis of the apparatus, and the patient vision along the optical axis is unobstructed. The patient's line of sight can be either a straight line or a polygonal chain formed by reflecting or refracting elements, such as mirrors, prisms, and the like. In the case of a polygonal chain line of sight, at least one segment of the polygonal chain line of sight can be coincident with the optical axis of the apparatus.)

Each of the two rotational units 18 and 22 is comprised of a set of three planet gears 10 that surround a central sun gear 30 to form a planetary gear mechanism. The sun gear 30 fixedly houses one of the rotatable optical elements 16 or 20. The planet gears each have a central stub shaft 32 extending normally from both of its planar faces, that is rotatably housed in hub bores 34, formed in the housing front panel 36 and rear panel 38. These prevent any translational motion of the planet gears and/or rotational motion about any axis other than the axis of the shaft (i.e. so as to prevent any motion of either of the lenses other than their parallel rotation about the common optical axis of the two optical elements).

The sun gear 30 has an inner perimeter groove 40 that the optical elements 16 or 20 are fixed into. The axis of rotation of the rotational unit 18 and 20 is coincident with the optical axis of the said optical element and is called the main rotational axis 100. Each of the two sun gears 30 are held in place by the three planet gears 10 that are in a fixed planetary configuration around it.

Each planet gear 10 possesses an external lip 46 on the outer perimeter of each side of the gear, which hugs the sun gear 30 and prevents any translational motion of the sun gear 30 (and optical element 16 or 20) in the direction along the rotational axis with respect to the planet gears that hold it and/or the rotational motion of the sun gear 30 about any axis other than the main rotational axis 100.

At least one planet gear 10 of each of the two sets of rotational units 18 and 22 has an axle 12 extending through the housing. This axle 12 is coupled to a rotational electric motor 44, either directly or through an optional additional gear transfer case. Thus, the rotatable units 18 and 22 and rotatable optical elements 16 and 20 can be rotated by the electric motors 44. There are two electric motors 44, with each controlling the rotation of one rotatable unit 18 or 22, independently of the other. Each of the two electric motors 44 receives simultaneous but independent electric control signals from the manual control input device 6. The manual control input device 6 is capable of receiving input through two (2) independent channels, each channel being controlled using an independent degree of freedom of the direct input device 6. In one exemplary embodiment, the input device is a trackball 98, which can be rotated by the user about two orthogonal axes, for example, left-right and forward-backward. Rotation of the trackball 98 about each of the orthogonal axes forms an input signal for each of the controlling channels. Each of the two (2) controlling channels can control one of the two (2) electric motors 44, thus determining the rotational position of one of the two rotational optical elements, 16 or 20, independently of the rotational position of the other optical element 20 or 16, respectively. As a result, the user can select any combination of angular positions of the two optical elements 16 and 20 by moving the trackball 98 to a position specific for that combination.

There are one or more angular scales 95 in each rotational unit 18 and 22 that allow measuring the angular position of the cylinder axis of each of the two optical elements 16 and 20. Alternatively, the said angular positions can be read electronically using devices having such a capability, such as servo motor, stepper motor, angular position sensor, or other device known in the industry. The combined readings of the angular positions of the optical elements 16 and 20 in conjunction with the information about the cylinder optical power of each of the optical elements 16 and 20 can be converted using mathematical formulae (or by reference to a relational database) into the magnitude of the cylinder optical power of the combined optical system comprised of the two optical elements and the orientation of the cylinder axis of the combined optical system.

To explain this function in more detail, the manual control input 6 has a tactile two-dimensional position sensor 98 and a microprocessor 90. There is at least one optical tracking (position) sensors that react to the two degrees of movement from the patient's tactile movement of the two-dimensional position sensor (herein trackball 98). This is regardless of whether it is a mouse, a trackpad, knobs with two degrees of freedom, a trackpoint, a track ball, a joystick, a touch screen or a functional equivalent. These signals of magnitude and direction are sent to the microprocessor 90. There is an internal circuit board that contains both software and hardware components necessary for processing input from the optical sensor (two dimension position sensor 98). This includes a microprocessor with memory that stores data about where each point on the position sensor 98 moved over time as well as functions like smoothing out any sudden movements or accelerating movement as the position sensor 98 moves more quickly. These signals are translated to output signals that are sent to the reversible stepping or servo motors that are operationally coupled to each optical element's rotational unit 18 or 22, so as to independently rotate each of the two lenses 16 and 20 with a direction and a magnitude (number of degrees of rotation).

There are two ways that the correct lens prescription for the patient is determined. There are rotary position sensors 92 operatively coupled to each sun gear 30 (or lens rotation mechanism18 and 22). Each lens's position is indexed to a rotational reference point. The rotary position sensors 92 provide signal feedback to the microprocessor as to the rotational position of the lenses. This feedback of each lens' rotational position is cross referenced to a relational database or is processed through an algorithm in a software program on the operating system of the microprocessor. Each combination of rotary positions of the two lenses 16 and 20 has been assigned, or can be computationally converted into, a prescription value for the total correction of the aberration for the eye and sends this prescription value to the video display 28.

Alternatively, the signal for the position of the position sensor 98, besides being used to generate drive signals to the motors to rotate the two lenses, can be used to determine the position of the lenses either algorithmically or by cross reference to a relational database found in the software or microprocessor memory and present it to the visual display 28 after the patient has found the particular combination of lens position that presents their best vision.

The advantage of this system is that is does not use discrete values of switchable lenses but rather has a continuous spectrum of corrective values that can be determined. This type of corrective lens determination is more accurate than discrete methods and, because of the use of a computer and automation, human error is practically eliminated resulting in an accuracy tolerance of up to 0.001.

In operation, the preferred embodiment of the astigmatism testing apparatus 2 involves a patient's use of a manual control input device 6 to control the rotary movement of rotatable optical elements 16 and 20 having cylindrical optical power, thus varying the rotary position of each of the two optical elements 16 and 20 to adjust the total cylindrical power and orientation of the cylinder axis of the combined elements. The preferred embodiment utilizes a trackball 98 as its tactile input mechanism, although an alternative input mechanism can be used, which can be capable of motion input in two or more degrees of freedom, with each degree of freedom of input controlling the rotary movement of a single cylindrical optical element 16 or 20 or both cylindrical optical elements 16 and 20 to adjust their total combined cylindrical power and the cylinder axis orientation. The embodiment can be supplemented with one or more spherical optical elements. Additional input degrees of freedom can be utilized to control the spherical power of the spherical optical element.

The procedure of optometry utilizing the apparatus, given by way of a non-limiting example of the procedure for the optometry of astigmatism, comprises the following steps. A patient views a test target (e.g., Snellen chart) with one eye, while the other eye is blocked, and a spherical corrective lens is determined by the practitioner to achieve the vision of the target of best acuity. This can be performed without or without the astigmatism testing apparatus 2 described herein being placed in front of the patient's eye. If the apparatus is placed in front of the patient's eye, it can be set to 0 diopter cylindrical optical power or to a best guess cylindrical optical power and angle of orientation based on objective refraction or previous known corrective glasses prescription. Then such a spherical corrective lens, together with the astigmatism testing apparatus 2 described herein, is placed in front of the patient's eye, on which the testing is performed, while the other patient's eye is blocked. The patient views a test target through the apparatus 2 along the apparatus's optical axis 100, while manipulating its optical parameters by providing input using a manual control input device 6 with two degrees of freedom. The manipulation of the two-dimensional input device controls two independent positional parameters of the device, namely the rotational positions of the optical elements of the device. This set of the positional parameters of the apparatus 2 uniquely corresponds to a set of optical parameters of the apparatus 2, namely the cylindrical optical power and the angular position of the cylinder axis. Thus, the patient can in real time continuously vary the said optical parameters of the apparatus 2 and can optimize his vision through the apparatus to achieve the maximum vision acuity. If the Snellen chart or other similar chart is used as a test target, the patient is instructed to attempt to achieve the readability of the characters of the smallest possible size.

As an alternative test target, a single or multiple bright emitting point sources of light may be used. Such a light source would be positioned similarly to any other test target, such as a Snellen chart—the light source would be in the patient's field of view while the patient looks down the optical axis of the apparatus. The luminosity of the light source should be at least 2 times as high as the luminosity of the background, however a higher ratio of the luminosity of the source to the luminosity of the background is preferred. Each light source should be at most 2 degrees of arc subtense in any direction as viewed by the patient, however a smaller arc subtense, 0.1 degrees or less, is preferred. If multiple sources of light are used, they should be separated from each other by at least 2 degrees of arc subtense as viewed by the patient, however a separation of 10 degrees or more is preferred. The shape of the light sources could be any rotationally symmetrical shape of order 3 or greater about the line of view, however a circular shape is preferred. Any color and type of light source, such as LED, luminescent, incandescent, dot matrix screen, or any other type, can be used. The shape of the light source can be defined by the light source itself or by placing an opaque screen with a transparent opening in front of the light source. In the case of an ideal vision of the patient, each point light source will be seen by the patient separate from the rest and without an elongation in any particular direction. In the case if the patient has uncorrected astigmatism, the source(s) of light will appear distorted, i.e. as a line or ellipse, rather than a point or circle. If this is the case, the patient is instructed to manipulate the manual control input device to attempt to achieve a vision where the light sources present themselves as points or circles, rather than lines or ellipses, of the smallest possible diameter, so as to best compensate the patient's astigmatism through operation of the device. Using such a light-based test target does not impact the manipulation of the apparatus.

When it is achieved, the practitioner may, optionally, make another iteration of the sphere correction, optionally followed by another iteration of astigmatism correction using the astigmatism testing apparatus 2. These iterations may be repeated any number of times, as needed. The condition thus determined corresponds to the patient's optimal correction of astigmatism. This, in turn, determines the unique set of optical parameters of the apparatus that provides the parameters of the corrective lens required to correct the patient's vision, namely the optical power and the angular position of the cylinder axis. A practitioner then takes the readings of the rotational positions of the optical elements of the apparatus 2 and uses the readings of the rotational positions of the optical elements 16 and 20 in conjunction with the information about the cylinder optical power of each of the optical elements 16 and 20 to calculate the cylindrical optical power of the compound optical system comprising the two optical elements 16 and 20 and the orientation of the cylinder axis of the compound optical system. The process of taking readings of the rotational positions of the optical elements 16 and 20 of the apparatus 2 and mathematical conversion into optical parameters can be further automated using electronic devices for data collection and calculation. This information is then used by the practitioner to prescribe the optical parameters of corrective glasses.

A similar approach can be used for the optometry of heterophoria, which is characterized by the polar angle of eye misalignment and the azimuthal angle of direction of misalignment. In the case of heterophoria, prismatic lenses should be used in place of cylindrical lenses comprising the apparatus, optionally supplemented with Maddox lens.

While certain features and aspects have been described with respect to exemplary embodiments, one skilled in the art will recognize that numerous modifications are possible. Moreover, while the procedures of the methods and processes for building, assembling and using the devices described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added, and/or subtracted from among other described embodiments, unless the context dictates otherwise. Consequently, although several exemplary embodiments are described above, it will be appreciated that the invention is intended to cover all modifications and equivalents within the scope of the following claims.

Having thus described the invention, what is claimed as new and desired to be secured by Letters Patent is as follows:

1. An optical testing apparatus operated solely by a patient without intermediation of an optometry practitioner for the determination of the patient's corrective glass prescription, comprising:

a housing rotatably holding a first lens of a first cylindrical power with respect to the light propagating along a first optical axis and a second lens of a second cylindrical power with respect to the light propagating along a second optical axis, wherein said first optical axis and second optical axis are aligned so as to be colinear;

a first lens angular scale indicating the rotational position of said first lens when brought into viewing focus by said patient;

a second lens angular scale indicating the rotational position of said second lens when brought into viewing focus by said patient;

a first motor connected to said first lens to rotate said first lens about said first optical axis with a first direction and a first magnitude;

a second motor connected to said second lens to rotate said second lens about said second optical axis with a second direction and a second magnitude;

a manually controlled input device adapted to adjust or control a combined optical power of a combination of said first and second lenses by providing a first drive signal to said first motor and a second drive signal to said second motor to rotate said first lens and said second lens independently and simultaneously wherein said manual control input device has a tactile two-dimensional position sensor selected from the group of position sensors consisting of mice, trackpads, knobs with two degrees of freedom, trackpoints, trackballs, joysticks, touch screens, and any other tactile sensor devices capable of accepting human input in at least two independent degrees of freedom each with independent variable magnitudes and operating in real time;

wherein said rotational position of said first lens and said rotational position of said second lens.

2. The optical testing apparatus of claim 1 wherein said first cylindrical power and said second cylindrical power may be identical, and wherein said first drive signal and said second drive signal may be provided simultaneously in absolute value but opposite in convergence and divergence.

3. The optical testing apparatus of claim 2, wherein said manual control input device further comprises:

a microprocessor with memory, a software program operating on said microprocessor, with said software program algorithmically generating said first drive signal and said second drive signal provided to said first motor and said second motor simultaneously based on a two-dimensional position signal, or two-dimensional position change signal, of said tactile two-dimensional position sensor.

4. The optical testing apparatus of claim 3, further comprising:

a first rotary position sensor capable of acquiring a value of a first rotational angle position of said first lens of a first cylindrical power; and a second rotary position sensor capable of acquiring a value of a second rotational angle position of said second lens of a second cylindrical power; and wherein said value of a first rotational angle position and said value of a second rotational angle position are communicated to said microprocessor for the calculation of a value for corrective eye glass prescriptive optical power and cylinder axis orientation.

5. The optical testing apparatus of claim 4, further comprising a visual or machine-readable output device capable of presenting or communicating a value for a prescriptive optical power and cylinder axis orientation based on calculated values provided by said microprocessor.

6. The optical testing apparatus of claim 1, further comprising:

a front viewing orifice providing unobstructed view through said housing along said first optical axis and second optical axis; and a rear viewing orifice providing unobstructed view through said housing along said first optical axis and second optical axis.

7. The optical testing apparatus of claim 1, further comprising:

a first rotational unit within said housing, said first rotational unit holding said first lens, said first rotational unit rotated in said first direction with said first magnitude by said first motor;

a second rotational unit within said housing, said second rotational unit holding said second lens, said second rotational unit rotated in said second direction with said second magnitude by said second motor.

8. An optical testing apparatus for the determination of corrective prescriptions, comprising:

a housing with a front wall and a rear wall held in a spaced configuration by at least one side wall, each front wall and rear wall;

a first lens of a first cylindrical optical power;

a second lens of a second cylindrical optical power;

a first rotational unit with an angular scale indicating the rotary position of said first lens, said first rotational unit translationally fixed in said housing by a first set of stub axles that extend from said first rotational unit into hubs formed in said front wall and said rear wall;

a second rotational unit with an angular scale indicating the rotary position of said second lens, said second rotational unit translationally fixed in said housing by a second stub axle that extends from said second rotational unit into said hubs;

said first lens mechanically engaged with and constrained by said first rotational unit;

said second lens mechanically engaged with and constrained by said second rotational unit;

an optical axis passing through a center of said first lens along the direction of its cylindrical optical power and a center of said second lens along the direction of its cylindrical optical power wherein both said rotational units are independently motor driven and coaxially aligned about a common optical axis;

a front viewing orifice in said front wall and a rear viewing orifice in said rear wall providing unobstructed view through said housing along said optical axis;

a first rotational shaft operably connected to said first rotational unit to rotate said first lens;

a second rotational shaft operably connected to said second rotational unit to rotate said second lens;

a tactile input device capable of input in two degrees of freedom simultaneously, independently and with varying magnitude, said tactile input device providing a drive signal to a first motor coupled to said first rotational shaft for rotation, and providing a drive signal to a second motor coupled to said second rotational shaft for rotation;

wherein said tactile input device is adapted to adjust or control the optical power of a combination of said first and second lenses by providing a first drive signal to said first motor and a second drive signal to said second motor to rotate said first lens and said second lens independently and simultaneously with real time synchronization between the position or the tactile input device and the optical characteristics of the combined system of said first and second lenses;

wherein said rotary position indicated by said angular scale of said first lens and said rotary position indicated by said angular scale of said second lens when brought into focus by a patient, is convertible by said patient into an optical prescription.

9. The optical testing apparatus of claim 8, wherein said first lens is fixed in a first rotatable sun gear and said second lens is fixed in a second rotatable sun gear; and wherein said first rotational unit is a first set of gears arranged in a planetary configuration comprised of a first sun gear and first planet gears that are translationally fixed in said housing by a first set of stub axles that extend from each of said first planet gears into first hubs formed in said front wall and said rear wall; and wherein said second rotational unit is a second set of gears arranged in a planetary configuration comprised of a second sun gear and second planet gears that are translationally fixed in said housing by a second set of stub axles that extend from each of said second planet gears into second hubs formed in said front wall and said rear wall; and wherein said first sun gear is mechanically engaged with and constrained by said set of first planet gears; and wherein said second sun gear is mechanically engaged with and constrained by said set of second planet gears.

10. The optical testing apparatus of claim 9 wherein said first rotational shaft and said second rotational shaft are rotated based on control signal by a tactile input device capable of input in two-dimensional space, selected from the group of tactile input devices consisting of trackpads, trackballs, computer mice, knobs with two degrees of freedom, joysticks, trackpoints, and touch screens, said tactile input device providing a drive signal to a first motor coupled to said first rotational shaft, and providing a drive signal to a second motor coupled to said second rotational shaft.

11. The optical testing apparatus of claim 10 further comprising:

a first rotary position sensor sensing the rotary position of said first optical element a providing a first position signal to said tactile input device;

a second rotary position sensor sensing the rotary position of said second lens a and providing a second position signal to said tactile input device;

a microprocessor in said tactile input device that interprets said first position signal and said second position signal and computes a total value for said corrective prescription.

12. An optometric apparatus for the measurement of astigmatism characteristics, comprising:

a structural frame or support that has at least one rigid element;

a first optical lens with first optical axis and a first toric refractive optical power or Jackson cross-cylinder refractive optical power in the direction of said first optical axis;

a second optical lens with second optical axis and second toric refractive optical power or Jackson cross-cylinder refractive optical power in the direction of said second optical axis;

wherein said first optical lens and said second optical lens are supported by said structural frame so as to prevent their translational motion or rotational motion except allowing the rotational motion of said first optical lens in the plane perpendicular to said first optical axis and allowing rotational motion of said second lens in the plane perpendicular to said second optical axis; and wherein said first optical lens and said second optical lens are spatially arranged so that there exists at least one straight line such that a light ray entering said optometric apparatus along that straight line would pass through both said first optical lens and said second optical lens and exit said optometric apparatus without being obstructed;

a first actuator controllable by a first electrical signal, with said first actuator being engaged with said first optical lens and being capable of causing and controlling its rotational motion in the plain perpendicular to said first optical axis;

a second actuator controllable by a second electrical signal, with said second actuator being engaged with said second optical lens and being capable of causing and controlling its rotational motion in the plain perpendicular to said second optical axis;

a tactile sensor adapted to be directly operated by said patient, capable of receiving input via human manipulation performed concurrently in two or more independent degrees of freedom, such as translational motion, rotational motion, or any combination thereof, and capable of simultaneously generating said two independent first and second control signals based on said input;

a microprocessor capable of receiving said control signals from said tactile sensor and sending electrical control signals to said first actuator and said second actuator simultaneously;

a software program operating on said microprocessor;

wherein said software program obtains said control signals from said tactile sensor, algorithmically processes said control signals, forms said first electrical signal and sends it to said first actuator, and forms said second electrical signal and sends it to said second actuator, simultaneously, independently of each other, and in real time, causing the combined optical characteristics of the system of said first and second lenses to be momentarily and continuously controlled by, and synchronized with, the position of the tactile sensor; and wherein said software program acquires a value of first angular position of said first optical lens by algorithmically processing a history of rotation of said first optical lens and acquires a value of second angular position of said second optical lens by algorithmically processing a history of rotation of said second optical lens, and wherein said software program algorithmically performs a calculation of optical parameters of the combined optical system comprised of said first optical lens and said second optical lens;

an output communication device capable of providing, in human-readable or machine-readable form, quantitative results of said calculation of optical parameters of the combined optical system.

13. The optometric apparatus of claim 12 further comprising:

a first rotary position sensor capable of acquiring a value of a first rotational angle position of said first optical lens; and a second rotary position sensor capable of acquiring a value of a second rotational angle position of said second optical lens;

wherein said software program is capable of receiving data of said first rotational angle position and said second rotational angle position and using said data to perform a calculation of optical parameters of the combined optical system comprised of said first optical lens and said second optical lens.

\* \* \* \* \*